United States Patent [19]

Hakky

[11] Patent Number: 4,773,423
[45] Date of Patent: Sep. 27, 1988

[54] BLOOD LOSS MEASUREMENT

[75] Inventor: Said I. Hakky, Largo, Fla.

[73] Assignee: Northstar Research Institute, Ltd., Philadelphia, Pa.

[21] Appl. No.: 40,518

[22] Filed: Apr. 17, 1987

[30] Foreign Application Priority Data

Apr. 18, 1986 [GB] United Kingdom ............... 8609582

[51] Int. Cl.⁴ .............................................. A61B 5/00
[52] U.S. Cl. ..................................... 128/637; 128/638
[58] Field of Search ................ 128/632, 637, 633, 638

[56] References Cited

U.S. PATENT DOCUMENTS 3,841,307 10/1974 Friedell ............................. 128/637
4,210,153 7/1980 Fehlau et al. ...................... 128/637
4,562,842 1/1986 Morfeld ............................. 128/638

Primary Examiner—Lloyd L. King
Attorney, Agent, or Firm—Caesar, Rivise, Bernstein, Cohen & Pokotilow, Ltd.

[57] ABSTRACT

Apparatus and method for measuring blood loss by collecting a blood sample from a patient prior to a surgical procedure, measuring the level of hemoglobin in that blood sample, collecting blood and pathological fluid removed from the patient during the surgical procedure; measuring the level of hemoglobin in the blood collected from the surgical procedure; comparing the level of hemoglobin in the blood collected prior to the surgical procedure with the level of hemoglobin in the blood after the surgical procedure and employing that comparison to determine the volume of blood lost during the surgical procedure.

14 Claims, 2 Drawing Sheets

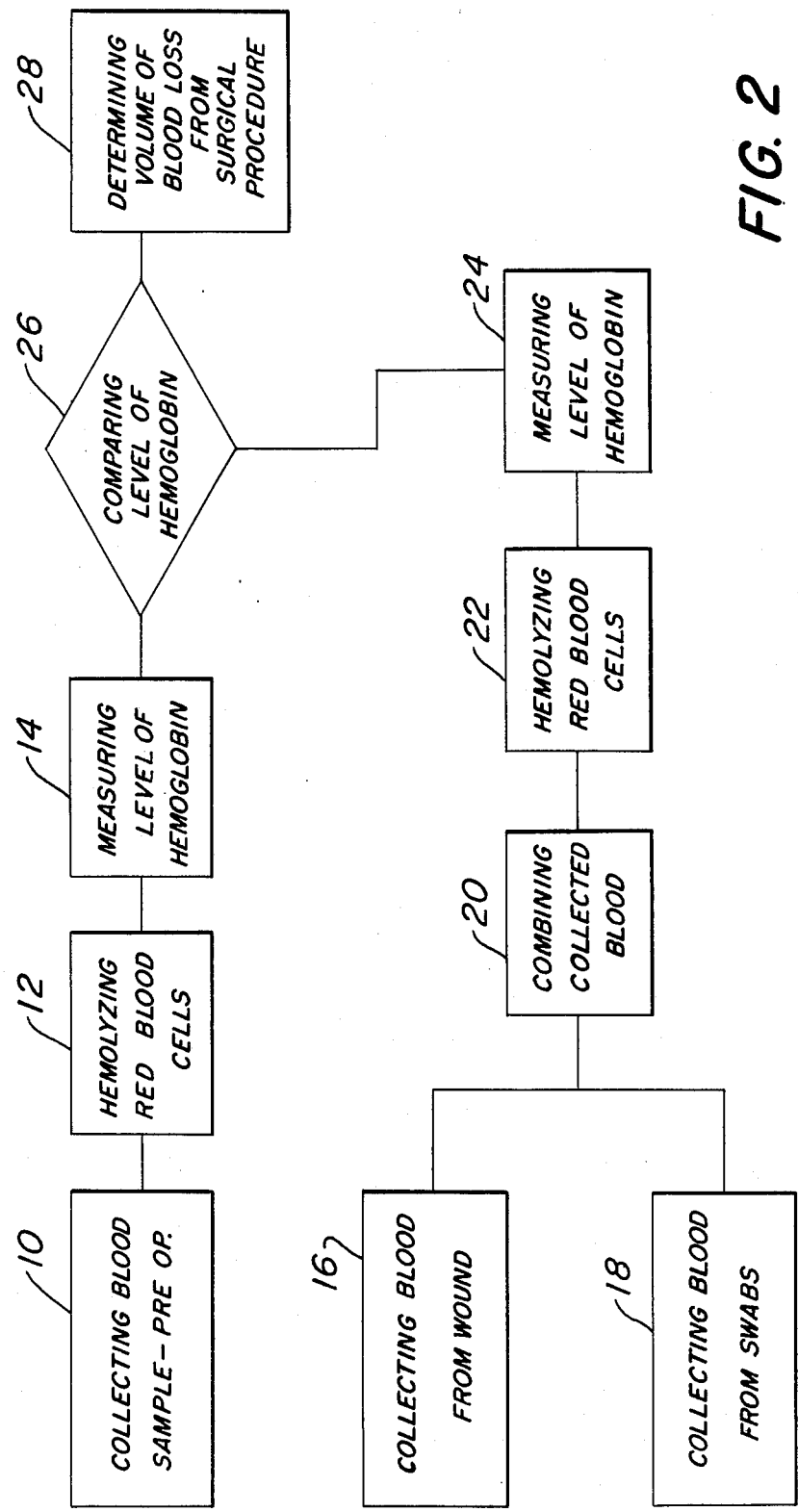

BLOOD LOSS MEASUREMENT

FIELD OF THE INVENTION

This invention relates generally to a method of determining blood loss, and more specifically, to a method of determining blood loss by a patient during a surgical procedure.

BACKGROUND ART

It is known that the loss of blood suffered by a patient during a surgical operation must be replaced. Blood together with pathological fluid or irrigation fluid is removed from an open wound by a surgical vacuum pipe into transparent bottles. The surgeon estimates the volume of blood in the bottle taking account of the other matter also passed to the bottle, e.g., pathological fluid, irrigational fluid and solid matter. a nurse weighs the used swabs to assess the volume of blood removed by swabbing the wound. The surgeon then replaces the amount of blood determined by the losses from both sources. It is important however, that the volume of blood lost be determined accurately. This is especially true in surgical procedures such as urology, e.g., transurethral resection of a large prostate when endoscopic surgery may mean that up to 20 litres of irrigation fluid may be needed to ensure visual clarity of the endoscopic field. It also is important to accurately determine the volume of blood loss in patients that are old, and frequently have compromised cardiovascular systems. For such patients it can be vital to replace exactly the volume of blood lost.

OBJECTS OF THE INVENTION

It is a general object of this invention to provide a method and apparatus for accurately determining the volume of blood loss by a patient in a surgical procedure.

It is a more specific object of this invention to accurately determine the volume of blood loss by a patient in a surgical procedure by taking into account the amount of blood actually lost through the surgical wound and also absorbed in surgical swabs.

SUMMARY OF THE INVENTION

The above and other objects of this invention are provided by an apparatus for use in determining the volume of blood loss during a surgical operation, wherein the apparatus comprises:
a first chamber to receive a sample of blood of the patient before the operation,
a second chamber to receive blood from the surgical wound,
a third chamber to receive used swabs and extract the blood therefrom;
means for measuring the level fo hemoglobin in the blood prior to the surgical procedure and in the blood collected from the surgical procedure; and
means for comparing the level of hemoglobin in the blood prior to the surgical procedure with that of the blood collected from the surgical procedure to determine the level of blood loss in the surgical procedure.

In accordance with the method of this invention the volume of blood loss during a surgical operation is determined by:
measuring the level of hemoglobin in the blood of the patient just before the operation,
collecting the blood and other matter from the surgical wound,
collecting the used swabs and recovering the blood therefrom,
hemolyzing the collected blood,
measuring the level of hemoglobin therein,
comparing the level of hemoglobin in the preoperation blood and the collected blood, and
determining the volume of collected blood from the comparison.

BRIEF DESCRIPTION OF THE DRAWINGS

Other objects and many of the attendant advantages of this invention will be readily appreciated as the same becomes better understood by reference to the following detailed description when considered in connection with the accompanying drawings wherein:

FIG. 2 is a schematic representation, in block form, showing the method steps employed in accordance with this invention for determining the volume of blood loss from a surgical procedure in accordance with this invention.

DESCRIPTION OF THE PREFERRED EMBODIMENTS OF THE INVENTION

Figure 1:
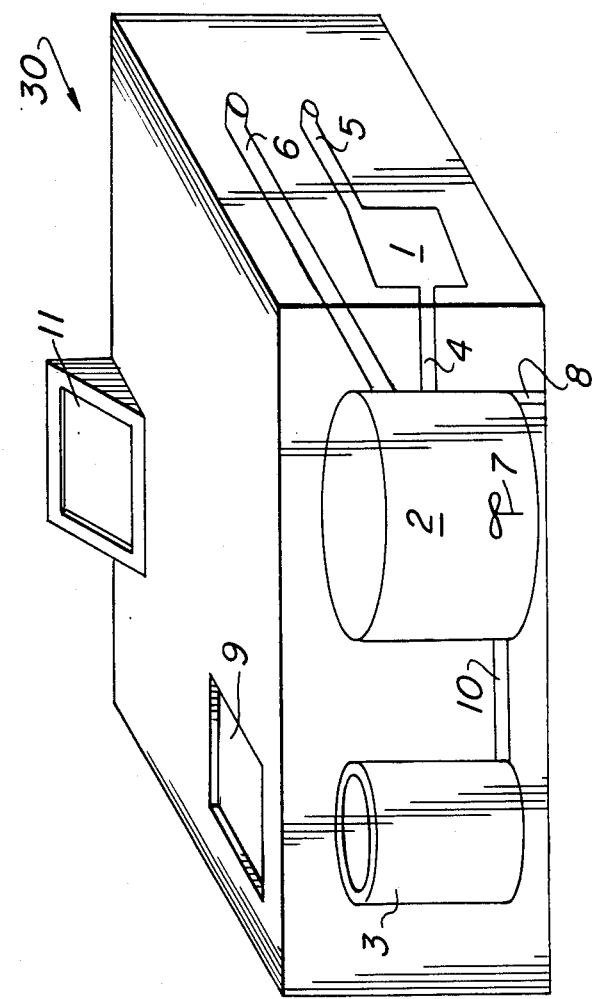
FIG. 1 is a schematic view of an apparatus employed to measure blood loss in accordance with this invention.

In accordance with this invention the concentration of blood is measured by means of the level of hemoglobin. This may be done in a variety of ways.

Hemoglobin is a prophyrin with one atom per hemoglobin molecule. The content of hemoglobin may be measured either by measuring the content of iron or the content of porphyrin. The iron content (which is in ferrous form), may be measured by any technique which does not register the content of ferric iron present in the blood serum. For example, the red blood cell capsules may be dissolved using a hemolyzing fluid (e.g., distilled water, ferricyanide). That solution is then diluted and mixed with a reagent (e.g., 2.2 dipyridyl, 2,2,2" tripyridyl, 1, 10- phenolthroline), and the colour of the resultant solution is then measured using a colorimeter. The ferrous iron may also be measured by nuclear magnetic resonance, analytic atomic spectroscopy, precipitation in chelate form followed by spectroscopic measurement of the precipitate. Porphyrins are fluorescent and may be detected and measured by fluorimetry or luminescence, either natural or chemically induced. Other ways of measuring the hemoglobin including measuring specific gravity and refractive index may also be suitable.

Referring to FIG. 2, the method in accordance with this invention is schematically illustrated in block form. In accordance with the preferred method the patient's blood initially is collected prior to performance of the surgical procedure (10). Thereafter the red blood cells are hemolyzed to liberate the hemoglobin therefrom (12) so that the level of heloglobin can be measured (14) by any of the the methods described earlier herein.

During the surgical procedure blood, along with other matter (e.g., pathological fluid, irrigational fluid and solid matter) is collected from the wound (16) and from swabs (18) employed during the procedure to clear the surgical sight, and are combined (20) into a single sample. Thereafter the combined sample is hemolyzed (22) to liberate the hemoglobin from the red blood cells, and the level of hemoglobin in the combined sample is then measured (24). Thereafter the level of hemoglobin in the pre-operational blood is compared with the level of the collected blood (26), and this comparison is employed to determine the volume of blood loss from the surgical procedure (28).

An apparatus for use in determining the volume of blood loss during a surgical procedure, and usable to carry out the method of this invention, is schematically illustrated in FIG. 1, and includes a housing 30 having three chambers 1, 2 and 3, respectively, and a digital readout device 11.

A conduit 5 leads from the chamber 1 to the exterior. The chamber 1 includes means, not shown, for measuring the hemopglobin content of blood. In a preferred form, the hemoglobin is reacted with a colorimetric reagent to yield a pink color, the intensity of which is measured by a colorimeter. The determination method will be appropriate to the property of the hemoglobin or its constiutent to be measured. Another conduit 6 leads from the exterior to the chamber 2. The chamber 2 is relatively much larger and is intended to receive blood, pathological fluid, etc., from the surgical wound via the conduit 6. An agitator 7 is present within the chamber 2 which also has an outlet 8 to waste. The chamber 3 is open at a hatch 9 in the top of the housing 30 and is designed to receive used surgical swabs. Means, not shown, are associated with the chamber 3 to compress the swabs to release the contained blood, which flows via a conduit 10 in the chamber 2. The chamber 3 may take the form of a high velocity rinse-drying machine, and also may include means to count the number of swaps received as a check that all of the used swabs are acounted for.

In use, a sample of blood is taken from a vein of the patient just before surgery, and passed in the chamber 1 to determine the content of hemoglobin. This information is then passed to the digital readout device 11. The hemoglobin concentration varies from 12 to 20 gm/decilitre, dependant on the patient's age, sex, nutritional and pathological status.

During the operation, blood sucked from the wound together with other matter drawn via the surgical vacuum pipe, (not shown) is passed down the conduit 6 to the chamber 2. The liquid is kept agitated by the agitator 7. Used swaps, (not shown), are placed via the hatch 9 in the the chamber 3, where the blood is urged out and passed via the conduit 10 to the chamber 2. Hemolyzing agent is added to separate the hemoglobin from the red blood cell capsules. A known volume of the sample of the total liquid in the chamber 2 at the end of surgery is passed via the conduit 4 to the chamber 1, where the hemoglobin level of the blood in the chamber 2 is determined. The value is then compared with the first reading, and the blood loss determined mathematically from the difference in hemoglobin contents. This deficiency in the blood volume is then added to the patient. In this way, the surgeon can check accurately and quickly the voluem of blood to be added to the patient. The invention is not limited to the embodiment shown. The patient may be human or animal.

Without further elaboration the foregoing will so fully illustrate my invention that others may, by applying current or future knowledge, adopt the same for use under various conditions of service.

What is claimed as the invention is:

1. A method of measuring loss of blood suffered by a patient during a surgical procedure including the steps of:
    (a) measuring the level of hemoglobin in the blood of the patient prior to the surgical procedure;
    (b) collecting the blood and other matter from a surgical wound during the surgical procedure;
    (c) measuring the level of hemoglobin in the blood collected from the surgical wound;
    (d) comparing the level of hemoglobin in the blood of the patient prior to the surgical procedure with the hemoglobin level in the blood collected from the surgical wound during the surgical procedure; and
    (e) determining the volume of collected blood from the comparison.

2. The method of claim 1 wherein the step of measuring the level of hemoglobin in the blood is carried out by measuring the content of iron in the red blood corpuscles.

3. The method according to claim 1 wherein the step of measuring the level of hemoglobin is carried out by measuring the content of porphyrin in the red blood corpuscles.

4. The method according to claim 1 wherein the red blood corpuscles in the collected blood are hemolyzed prior to measuring the level of hemoglobin therein.

5. The method according to claim 2 wherein the iron content is determined by hemolyzing the red blood corpuscles in a hemolyzing fluid and measuring the color of the hemolyzed red corpuscles, said color being representative of the level of iron in the hemolyzed solution.

6. The method of claim 2 including the step of measuring the content of ferrous iron in the red corpuscles by nuclear magnetic resonance, analytic atomic spectroscopy or precipitation in chelate form followed by spectroscopic measurment of the precipitate.

7. The method of claim 3 wherein the step of determining the level of prophyrin is carried out by measuring the fluorescence or luminescence of said porphyrin.

8. The method according to claim 4 wherein the level of hemoglobin is determined by measuring either the specific gravity or refractive index of hemolyzed collected red blood corpuscles.

9. The method according to claim 1 wherein the step of collecting blood from the surgical procedure is carried out by collecting blood directly from the surgical wound and also from swabs employed in the surgical procedure.

10. The method according to claim 9 wherein the swabs used in the surgical procedure are placed in a chamber from which the blood is extracted, said chamber communicating with a second chamber in which blood directly from the surgical wound is directed, the level of hemoglobin in the collected blood being determined after the blood from the swabs has been combined with the blood received directly from the surgical wound.

11. An apparatus for measuring loss of blood suffered by a patient during a surgical procedure, said apparatus comprising:
    (a) a first chamber for receiving a sample of blood of the patient prior to performance of the surgical procedure;
    (b) a second chamber for receiving blood from a surgical wound of the patient;
    (c) a third chamber for receiving used swabs employed in the surgical procedure, said third chamber including means for extracting blood from said swabs;

(d) means for measuring the level of hemoglobin in the blood collected from the patient prior to the surgical procedure;

(e) means for measuring the level of hemoglobin in the blood collected from the surgical wound and from the swabs; and (f) means for comparing the level of hemoglobin in the blood collected from the patient prior to the surgical procedure with the level of hemoglobin in the blood collected from both the surgical wound and the swabs for determining the amount of blood loss resulting from the surgical procedure.

12. The apparatus of claim 11 including passage means for communicating the third chamber with said second chamber for permitting the blood extracted from the swabs in the third chamber to be directed into said second chamber; said means for measuring the level of hemoglobin in the blood obtained from the surgical procedure and from the swabs being employed to measure the level of hemoglobin in the blood in the second chamber, after the blood from the swabs has been transmitted to the second chamber from said third chamber.

13. The apparatus of claim 11 further including means for counting the swabs received in the third chamber to permit a comparison of the number of swabs placed in the third chamber with the number of swabs used in the surgical procedure.

14. The apparatus of claim 11 including a digital readout for displaying the quantity of blood lost by a patient during the surgical procedure.

* * * * *